United States Patent [19]

Angres et al.

[11] 4,172,088
[45] Oct. 23, 1979

[54] BIS(2-FLUORO-2,2-DINITROETHYL)TH-IONOCARBONATE AND A METHOD OF PREPARATION

[75] Inventors: Isaac A. Angres, Gaithersburg; Horst G. Adolph, Silver Spring, both of Md.; William Gilligan, Washington, D.C.

[73] Assignee: The United States of America as represented by the Secretary of the Navy, Washington, D.C.

[21] Appl. No.: 918,122

[22] Filed: Jun. 22, 1978

[51] Int. Cl.² .......................................... C07C 154/00
[52] U.S. Cl. .................................................. 260/455 R
[58] Field of Search .................................... 260/455 R

[56] References Cited

U.S. PATENT DOCUMENTS

| | | | |
|---|---|---|---|
| 3,306,939 | 2/1967 | Hill | 568/590 |
| 3,388,147 | 6/1968 | Kamlet | 260/463 |
| 3,396,187 | 8/1968 | Benziger et al. | 260/463 |
| 3,553,273 | 1/1971 | Adolph et al. | 568/712 |
| 3,751,476 | 8/1973 | Adolph et al. | 260/583 CC |
| 3,845,104 | 10/1974 | Gilligan | 560/156 |
| 3,845,105 | 10/1974 | Gilligan | 560/156 |
| 3,846,493 | 11/1974 | Gilligan | 260/561 N |
| 3,922,311 | 11/1975 | Peters et al. | 568/590 |
| 3,992,432 | 11/1976 | Napier | 260/465.1 |
| 4,001,291 | 1/1977 | Adolph | 260/455 R |

OTHER PUBLICATIONS

Starks, J.A.C.S., vol. 93:1, (Jan. 13, 1971), pp. 195–199 (Starks).

Dehmlow, Angew Chem., Internat. Edit., vol. 13, (1947), No. 3, pp. 170–177.
Dehmlow, Chemtech, Apr. 1975, pp. 210–218 (Dehmlow).

*Primary Examiner*—Alan L. Rotman
*Assistant Examiner*—Robert C. Whittenbaugh
*Attorney, Agent, or Firm*—R. S. Sciascia; A. L. Branning; R. D. Johnson

[57] ABSTRACT

Novel bis(2-fluoro-2,2-dinitroethyl)thionocarbonate,

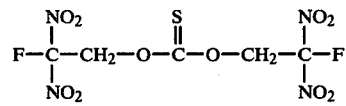

is prepared from two moles of 2-fluoro-2,2-dinitroethanol and two equivalents of a strong hydroxyl ion source such as sodium hydroxide or potassium hydroxide in water and one mole of thiophosgene in an organic solvent which may be methylene chloride, chloroform, or 1,2-dichloroethane. A phase transfer catalyst which may be benzyltriethylammonium chloride, tetrabutylammonium chloride, didodecyldimethylammonium bromide, or cetyltrimethylammonium chloride is used to transfer 2-fluoro-2,2-dinitroethoxy ions formed in the water phase to the organic solvent phase where they react with the thiophosgene to form the bis(2-fluoro-2,2-dinitroethyl)thionocarbonate. Bis(2-fluoro-2,2-dinitroethyl)thionocarbonate is useful as an energetic explosive.

3 Claims, No Drawings

BIS(2-FLUORO-2,2-DINITROETHYL)THIONOCARBONATE AND A METHOD OF PREPARATION

SUMMARY OF THE INVENTION

Accordingly, one object of this invention is to provide a novel chemical compound.

A further object of this invention is to provide a novel energetic explosive compound.

Yet another object of this invention is to provide a novel method of synthesizing a chemical compound.

These and other objects of this invention are accomplished by providing bis(2-fluoro-2,2-dinitroethyl)thionocarbonate,

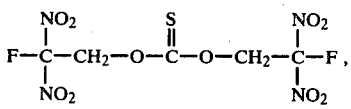

which is prepared from two moles of 2-fluoro-2,2-dinitroethanol and two equivalents of a strong hydroxyl ion source such as sodium hydroxide or potassium hydroxide in water and one mole of thiophosgene in an organic solvent selected from the group consisting of methylene chloride, chloroform, and 1,2-dichloroethane. A phase transfer catalyst selected from the group consisting of benzyltriethylammonium chloride, tetrabutylammonium chloride, didodecyldimethylammonium bromide, and cetyltrimethylammonium chloride is used to transfer 2-fluoro-2,2-dinitroethoxy ions formed in the water phase to the organic solvent phase where they react with the thiophosgene to form the bis(2-fluoro-2,2-dinitroethyl)thionocarbonate. Bis(2-fluoro-2,2-dinitroethyl)thionocarbonate is useful as an energetic explosive.

DETAILED DESCRIPTION OF THE PREFERRED EMBODIMENT

A standard method of preparing thionocarbonates is by the reaction of two moles of an alcohol and two equivalents of a strong hydroxyl ion source such as sodium hydroxide or potassium hydroxide in water with one mole of water-insoluble thiophosgene. When 2-fluoro-2,2-dinitroethanol is used, the reaction proceeds slowly, requiring up to 2½ hours to form bis(2-fluoro-2,2-dinitroethyl)thionocarbonate. This is probably the result of solvation of the alcohol anion as well as the insolubility of the thiophosgene in water. Unfortunately 2-fluoro-2,2-dinitroethoxy ions easily decompose in the presence of strong hydroxyl ion sources such as sodium hydroxide or potassium hydroxide. Therefore long exposure time in this standard process results in a poor yield of bis(2-fluoro-2,2-dinitroethyl)thionocarbonate.

It has been found, however, that the reaction can be greatly speeded up by dissolving the thiophosgene in an organic solvent and by using a phase transfer catalyst to transfer 2-fluoro-2,2-dinitroethoxy ions from the water phase to the organic solvent phase. Thus, in example 1 the use of an organic solvent and a phase transfer catalyst reduced the time required to produce bis(2-fluoro-2,2-dinitroethyl)thionocarbonate to 15 minutes and increased the yield to 90 percent. The reduction in reaction time appears to be due to the greater reactivity of the 2-fluoro-2,2-dinitroethoxy ion in the organic phase and the increased contact between the ethoxy ions and the thiophogene.

Phase transfer catalysts such as benzyltriethylammonium chloride, tetrabutylammonium chloride, didodecyldimethylammonium bromide, or cetyltrimethylammonium chloride may be used in the process of this invention. The phase transfer catalyst is not consumed by the reaction; therefore only a small amount, a few mole percent, of the phase transfer catalyst is required.

Good discussions about the use of phase transfer catalysts are presented by Charles M. Starks, "Phase Transfer Catalysts. I. Heterogeneous Reactions Involving Anion Transfer by Quaternary Ammonium and Phosphonium Salts," Journal of the American Chemical Society, Volume 93:1, Jan. 13, 1971, pages 195–199, and by Echehard V. Dehmlow, "Phase-Transfer Catalyzed Two-Phase Reactions in Preparative Organic Chemistry," Angew. Chem. internat Edit. volume 13 (1974)/No. 3, Pages 170–178, adapted in Chemtech, April 1975, pages 210–218.

In the present process methylene chloride was found to work well as the solvent for the organic phase. Similar solvents, such as chloroform and 1,2-dichloroethane should also be suitable.

Aqueous hydroxide, preferably from about 25 to about 50 percent by weight, is slowly added to the reaction mixture. By means of this slow addition and external cooling, the reaction temperature is kept below room temperature (25° C.) and preferably in the range of from 0° C. to 5° C. Two equivalents of hydroxide ions are consumed for each mole of the thiophosgene. Upon completion of the reaction the reaction mixture changes in color from red (due to thiophosgene) to clear.

The general nature of the invention having been set forth, the following example is presented as a specific illustration thereof. It will be understood that the invention is not limited to this specific example but is susceptible to various modifications that will be recognized by one of ordinary skill in the art.

EXAMPLE 1 bis(2-fluoro-2,2-dinitroethyl)thionocarbonate

To a solution of 20 ml of 2-fluoro-2,2-dinitroethanol in 40 ml of methylene chloride, 1.0 g of benzyltriethylammonium chloride, 25 ml of water, and 8 ml of thiophosgene were added. The resultant mixture was cooled to 0° C. and 10.7 ml of 50% sodium hydroxide were added dropwise (maintaining the temperature between 0° C. and 5° C.) until the red color of the thiophosgene was discharged. Once the red color was discharged (about 15 minutes), 200 ml of hexane were added and the mixture was filtered. A light yellow product was obtained, m.p. 80°–88° C. The yield was 31 g (90% of the theoretical). The product was recrystallized from hexane to give white needles, m.p. 94° C.–96° C.; nmr in acetone-$d_6$ shows a doublet at $\delta$ 5.45 ppm.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the U.S. is:

1. Bis(2-fluoro-2,2-dinitroethyl)thionocarbonate.

2. A method of preparing bis(2-fluoro-2,2-dinitroethyl)thionocarbonate comprising:
(1) forming a two phase reaction mixture comprising
   (a) an aqueous phase comprising
      (i) 2-fluoro-2,2-dinitroethanol, and
      (ii) water; and
   (b) an organic solvent phase comprising
      (i) thiophosgene,
      (ii) a phase transfer catalyst selected from the group consisting of benzyltriethylammonium chloride, tetrabutylammonium chloride, didodecyldimethylammonium bromide, and cetyltrimethylammonium chloride, and
      (iii) an organic solvent selected from the group consisting of methylene chloride, chloroform, and 1,2-dichloroethane;
(2) slowly adding a 25 to 50 percent aqueous solution of a strong hydroxyl ion source to the reaction mixture with stirring and cooling of the reaction mixture to prevent the reaction temperature from rising above room temperature; and
(3) isolating the product bis(2-fluoro-2,2-dinitroethyl)thionocarbonate;
Provided that for each mole of thiophosgene used about 2 moles of 2-fluoro-2,2-dinitroethanol and about 2 equivalents of strong hydroxyl ion source are used.

3. The method of claim 2 wherein the temperature of the two phase reaction mixture is kept in the range of from 0° C. to 5° C.

* * * * *